US008894649B2

(12) United States Patent
Lee, Jr. et al.

(10) Patent No.: US 8,894,649 B2
(45) Date of Patent: Nov. 25, 2014

(54) EXTERNAL FIXATION SYSTEM

(71) Applicant: 3D Medical Concepts, LLC, Pelham, AL (US)

(72) Inventors: Harry E. Lee, Jr., Birmingham, AL (US); Joshua J. Reardon, Tuscaloosa, AL (US); Beverly L. Laird, Birmingham, AL (US)

(73) Assignee: 3D Medical Exfix, LLC, Pelham, AL (US)

( * ) Notice: Subject to any disclaimer, the term of this patent is extended or adjusted under 35 U.S.C. 154(b) by 38 days.

(21) Appl. No.: 13/733,682

(22) Filed: Jan. 3, 2013

(65) Prior Publication Data

US 2014/0025076 A1 Jan. 23, 2014

Related U.S. Application Data

(63) Continuation of application No. 61/582,996, filed on Jan. 4, 2012.

(51) Int. Cl.
*A61B 17/56* (2006.01)
*A61B 17/64* (2006.01)

(52) U.S. Cl.
CPC ......... *A61B 17/6466* (2013.01); *A61B 17/6433* (2013.01)
USPC .......................................................... 606/59

(58) Field of Classification Search
CPC ............... A61B 17/6466; A61B 17/66; A61B 17/6416; A61B 17/645; A61B 17/6425; A61B 17/6458
USPC ...................................................... 606/57–59
See application file for complete search history.

(56) References Cited

U.S. PATENT DOCUMENTS

| | | | |
|---|---|---|---|
| 2,391,693 A | 12/1945 | Ettinger | |
| 4,730,608 A | 3/1988 | Schlein | |
| 4,890,631 A | 1/1990 | Hardy | |
| 5,403,316 A | 4/1995 | Ashman | |
| 5,443,464 A * | 8/1995 | Russell et al. | 606/54 |
| 5,451,225 A | 9/1995 | Ross, Jr. et al. | |
| 5,676,664 A | 10/1997 | Allard et al. | |
| 8,216,288 B2 | 7/2012 | Lee et al. | |
| 2005/0101959 A1 | 5/2005 | Mitkovic | |

* cited by examiner

*Primary Examiner* — Mary Hoffman
*Assistant Examiner* — Tara Carter
(74) *Attorney, Agent, or Firm* — Bush Intellectual Property Law; Kenneth M. Bush

(57) ABSTRACT

An external fixation system having at least one ball collet pivotably mounted within a movable clamp and at least one ball collet pivotably mounted within a fixed clamp, wherein a surgical pin is mounted within each ball collet. In operation, the surgical pins are screwed into bone and passed through openings through the fixed clamp, movable clamp, and ball collets. A drive knob is operable to rotate a drive screw and thereby move the movable clamp either towards or away from the fixed clamp and concomitantly move the pins secured in the movable clamp either towards or away from the pins secured in the fixed clamp. A connecting rod prevents axial rotation of the movable clamp and fixed clamp relative to each other.

6 Claims, 14 Drawing Sheets

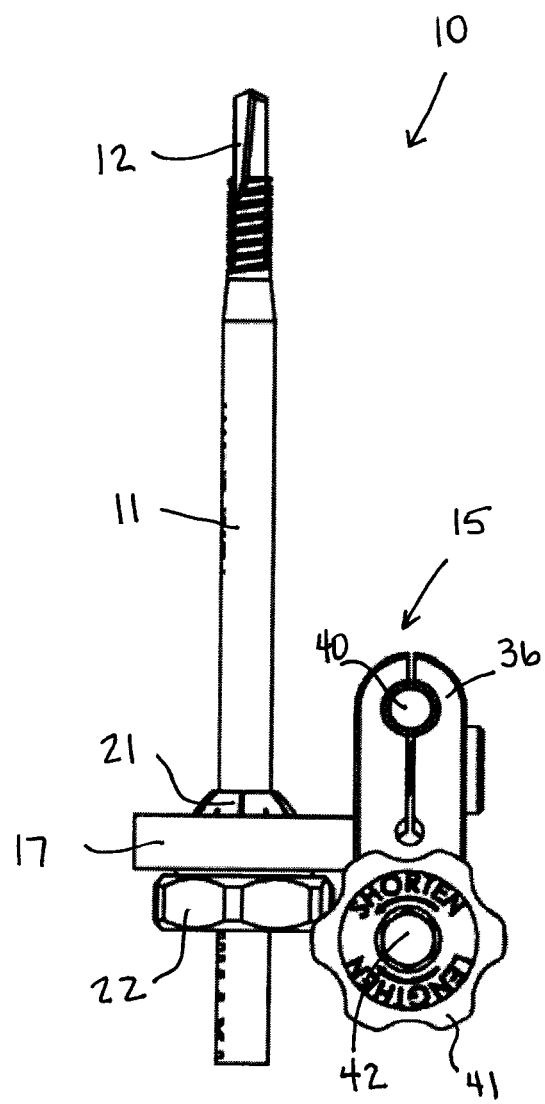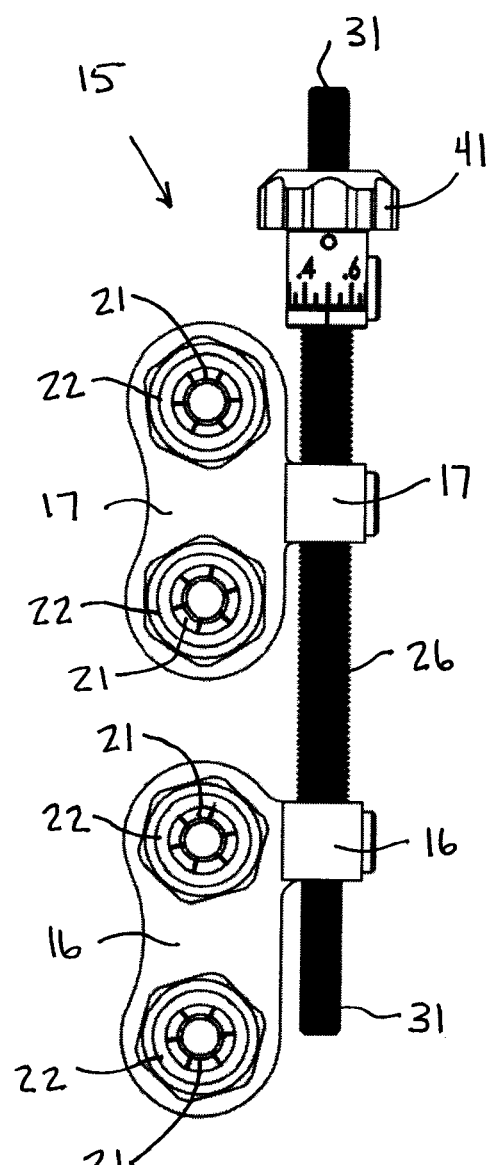
FIG. 17
FIG. 18

EXTERNAL FIXATION SYSTEM

CROSS-REFERENCE TO RELATED APPLICATION

The present application claims priority to U.S. Provisional Patent Application No. 61/582,996, filed Jan. 4, 2012, the disclosure of which is incorporated herein by reference.

FIELD OF THE INVENTION

The present invention relates to medical devices, and more particularly, to an external fixation system for stabilizing a bone fracture.

BACKGROUND OF THE INVENTION

External fixation systems are used for a number of medical purposes, such as to treat certain bone fractures, for bone lengthening procedures, and to correct certain bone deformations. These fixation systems are used by inserting a plurality of surgical pins through the skin and into the bone on each side of a bone fracture. The pins are attached to an external frame assembly to provide stability and proper alignment of bone fragments during the healing process. These surgical pins may remain in position for several days, weeks, or even months, depending upon the severity of the fracture and other factors. The present invention is an improvement to such external fixation systems.

SUMMARY OF THE INVENTION

According to a preferred embodiment of the present invention, the invention is an external fixation system comprising a plurality of surgical pins, a plurality of ball collets, a plurality of collet caps, a drive screw, a connecting rod, a cap clamp having a first hole for receiving the upper end of the drive screw therethrough and a second hole for receiving the connecting rod therethrough, a movable clamp having a first hole for receiving the body of the drive screw therethrough and a second hole for receiving the connecting rod therethrough and a first opening for receiving a surgical pin therethrough, a fixed clamp having a first hole for receiving the lower end of the drive screw therein and a second hole for receiving the connecting rod therethrough and a first opening for receiving a surgical pin therethrough, and a drive knob having a hole for receiving the upper end of the drive screw therein wherein the drive knob is secured to the drive screw for concomitant rotation therewith.

A first ball collet is pivotably mounted within the movable clamp first opening, wherein the first ball collet is secured within the movable clamp first opening by a first collet cap reversibly attached to the movable clamp, and wherein a first surgical pin is pivotably mounted within the first ball collet. A second ball collet is pivotably mounted within the fixed clamp first opening, wherein the second ball collet is secured within the fixed clamp first opening by a second collet cap reversibly attached to the fixed clamp, and wherein a second surgical pin is pivotably mounted within the second ball collet. A third ball collet is pivotably mounted within a movable clamp second opening, wherein the third ball collet is secured within the movable clamp second opening by a third collet cap reversibly attached to the movable clamp, and wherein a third surgical pin is pivotably mounted within the third ball collet. A fourth ball collet is pivotably mounted within a fixed clamp second opening, wherein the fourth ball collet is secured within the fixed clamp second opening by a fourth collet cap reversibly attached to the fixed clamp, and wherein a fourth surgical pin is pivotably mounted within the fourth ball collet.

In operation, first ends of the surgical pins are preferably screwed into fractured bone and the second ends of the pins are passed through openings through the fixed clamp and movable clamp, the ball collets, and the collet caps. The collet caps are tightened to compress the ball collets and thereby secure the pins within the ball collets. The drive knob can be rotated clockwise or counterclockwise to rotate the drive screw and thereby move the movable clamp either towards or away from the fixed clamp and concomitantly move the pins through the movable clamp either towards or away from the pins through the fixed clamp.

A principal feature of the invention is the connecting rod. The connecting rod is preferably splined to provide excellent transport geometry and prevent the movable and fixed clamps from axial rotation relative to each other. This novel feature has application in other external fixation systems, such as simple unilateral frame assemblies utilizing single pin clamps and/or double pin clamps, or in a ring-type frame assembly (e.g., an "Ilizarov" device). Another principal feature of the invention is the collet feature, wherein use of the ball collets allows for an expanded area for surgical pin placement and enhances the accuracy of pin placement, with each pin having an independent range of motion.

These and other features of the invention will become apparent from the following detailed description of the invention.

BRIEF DESCRIPTION OF THE DRAWINGS

FIG. 17 is a top plan view of the embodiment of FIG. 14.
FIG. 18 is a front elevational view of the embodiment of FIG. 14.

DETAILED DESCRIPTION OF THE INVENTION

Figure 1:
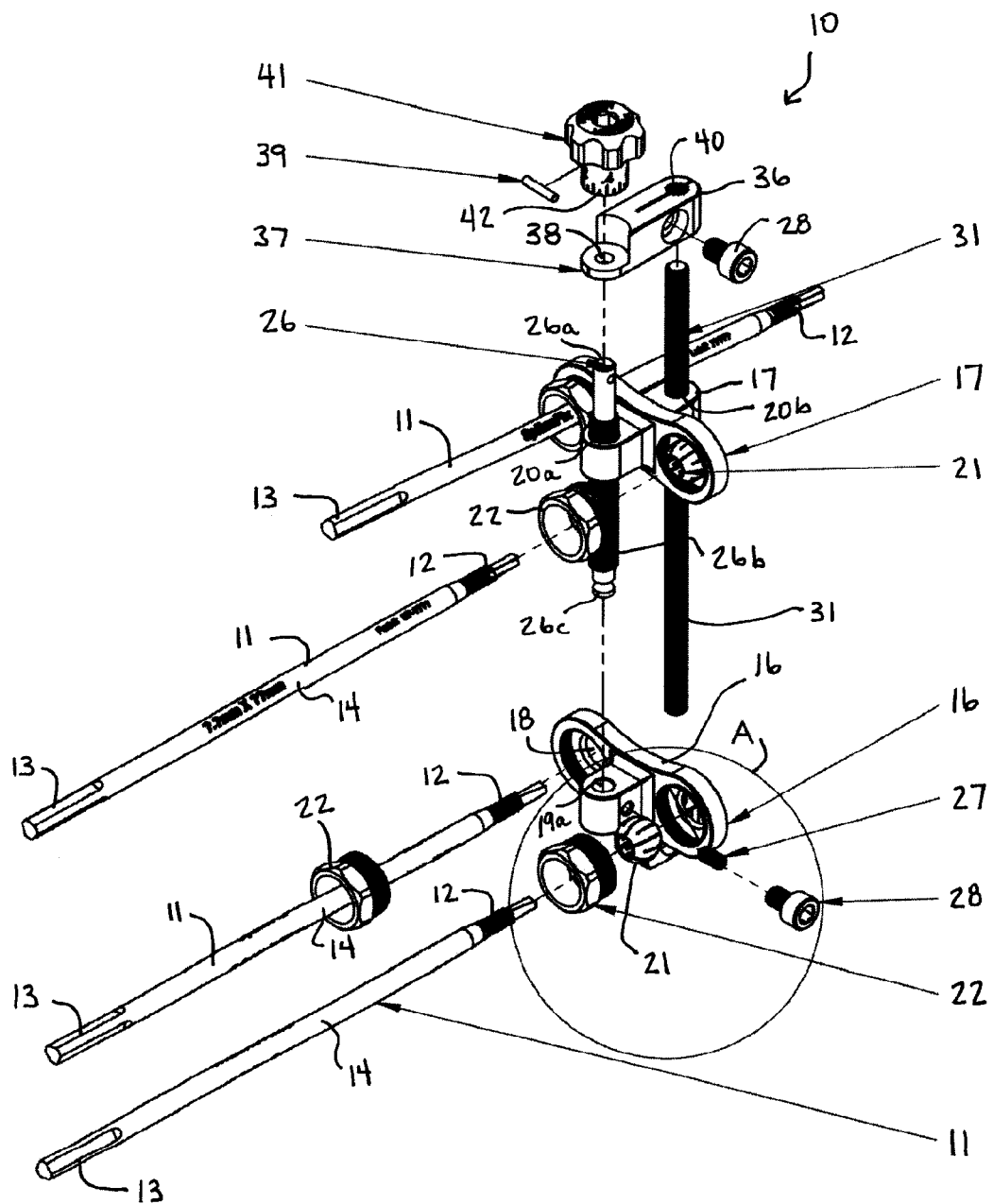
FIG. 1 is an exploded front perspective view of the present invention.
Figure 2:
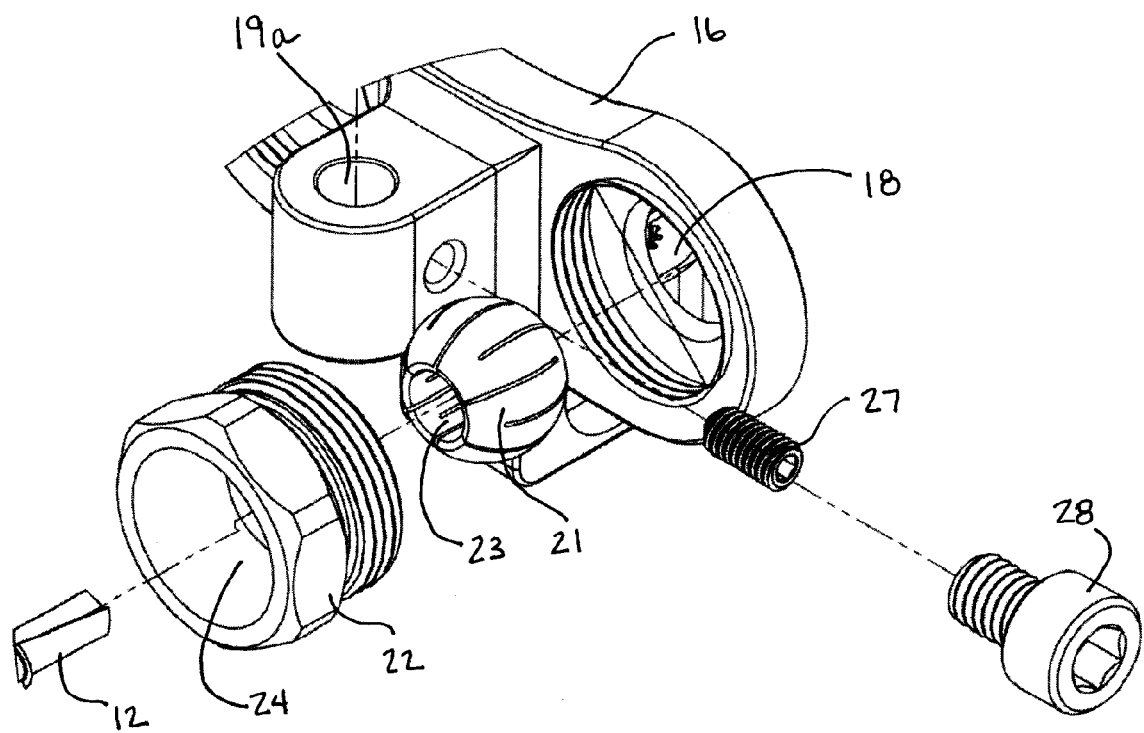
FIG. 2 is a detail view of area A in FIG. 1.
Figure 3:
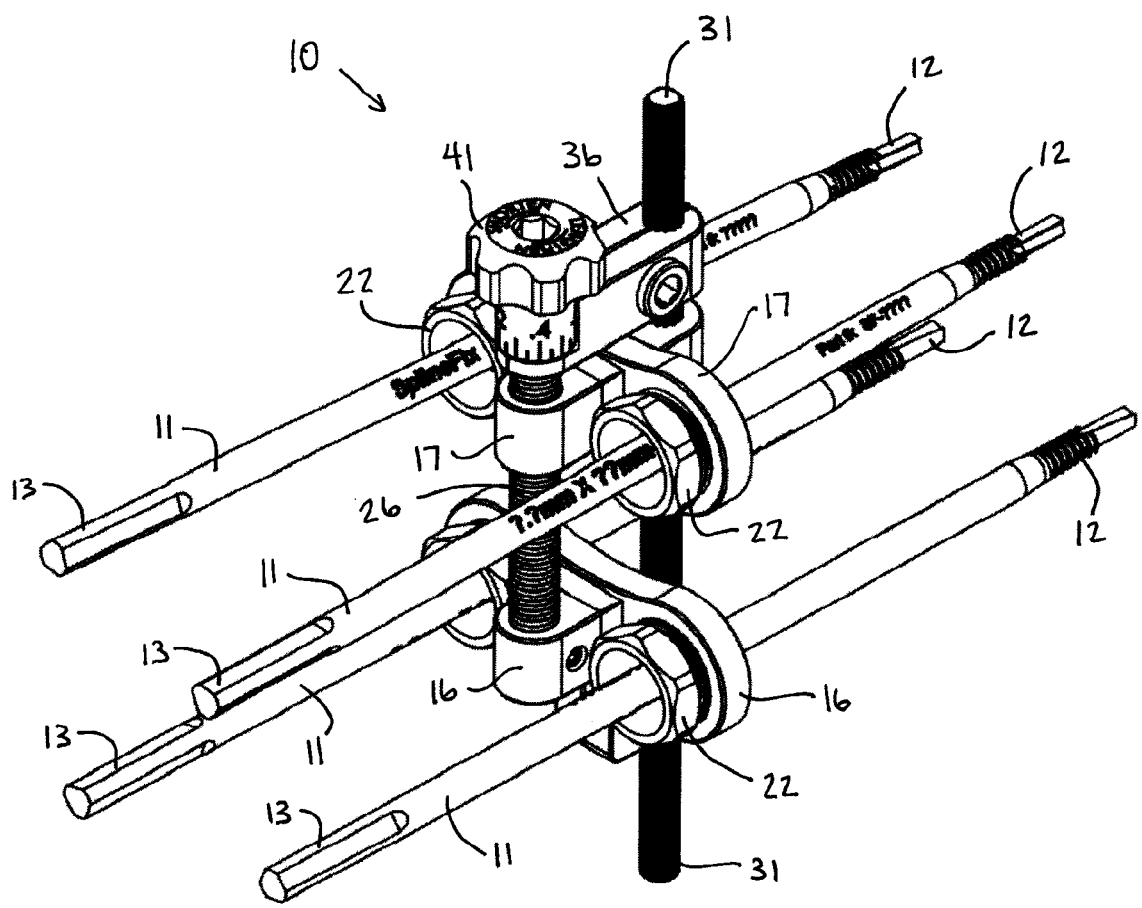
FIG. 3 is a right front perspective view of the present invention.

The preferred embodiments of the present invention are shown in FIGS. 1-20, wherein the invention comprises an external fixation apparatus 10 having a plurality of surgical pins 11, wherein each pin 11 has a first end 12 that is secured directly to bone, an opposing second end 13, and an elongated body 14 that is secured within an external frame assembly 15. The frame assembly 15 preferably comprises a fixed clamp 16 and a movable clamp 17, wherein each clamp 16, 17 has at least one opening 18 therethrough with a ball collet 21 pivotably mounted therein and secured therein by a collet cap 22.

The ball collet 21 has an opening 23 therethrough that aligns with an opening 24 through the collet cap 22. The fixed clamp 16 and movable clamp 17 are secured to each other on a front side with a drive screw 26 and on a rear side with a connecting rod 31 preferably having a plurality of splines 32 extending the length thereof ("splined connector"). The drive screw 26 and splined connector 31 are maintained in parallel relationship to each other.

The drive screw 26 has an unthreaded upper end 26a, a threaded body 26b, and an unthreaded lower end 26c. The fixed clamp 16 has an unthreaded first channel or hole 19a for receiving the unthreaded lower end 26c of drive screw 26 therein and a grooved second hole 19b for receiving the splined connector 31 therethrough. The fixed clamp 16 can be secured to the unthreaded lower end 26c of drive screw 26 with a drive screw retainer 27 and a socket head cap screw 28 that allows the drive screw 26 to rotate within fixed clamp 16. The movable clamp 17 has a threaded first hole 20a for receiving the threaded body 26b of the drive screw 26 therethrough and a grooved second hole 20b for receiving the splined connector 31 therethrough. The movable clamp 17 can be threadably secured to the threaded body 26b of drive screw 26. A cap clamp 36 has a ring member 37 with an unthreaded first hole 38 for receiving the upper end 26a of drive screw 26 therethrough, wherein a dowel pin 39 preferably secures the cap clamp 36 to the drive screw 26. The cap clamp 36 has a grooved second hole 40 for receiving the splined connector 31 therethrough, wherein the cap clamp 36 can be immovably secured to the splined connector 31 with a socket head cap screw 28. A drive knob 41 has a hole 42 for receiving the unthreaded upper end 26a of drive screw 26 therein, wherein the drive knob 41 can be secured to the unthreaded upper end 26a of drive screw 26 for concomitant rotation therewith. The fixation apparatus 10 is MRI compatible, lightweight, and has a low profile design for convenient use.

In operation, the first ends 12 of the pins 11 are preferably screwed into fractured bone and the second ends 13 of the pins 11 are passed through the openings 18, 23, 24 through the fixed clamp 16 and movable clamp 17, the ball collets 21, and the collet caps 22. The collet caps 22 are tightened to compress the ball collets 21 and thereby secure the pins 11 within the ball collets 21. The drive knob 41 can be rotated clockwise or counterclockwise to rotate the drive screw 26 and thereby move the movable clamp 17 either towards (e.g. compression procedure) or away from (e.g. lengthening procedure) the fixed clamp 16 and concomitantly move the pins 11 through the movable clamp 17 either towards or away from the pins 11 through the fixed clamp 16. The splined connector 31 prevents the movable clamp 17 and the fixed clamp 16 from axial rotation relative to each other.

A principal feature of the invention is the splined connection feature. The splined connector 31 provides excellent transport geometry and prevents the clamps 16 and 17 from rotating relative to each other. This novel feature has application in other external fixation systems, for example, in simple unilateral frame assemblies utilizing single pin clamps 51 and/or double pin clamps 52 (see FIGS. 19 and 20), or in a ring-type frame assembly (e.g., an "Ilizarov" device) such as that described in U.S. Pat. No. 4,890,631 to Hardy, the disclosure of which is incorporated herein by reference.

Figure 4:
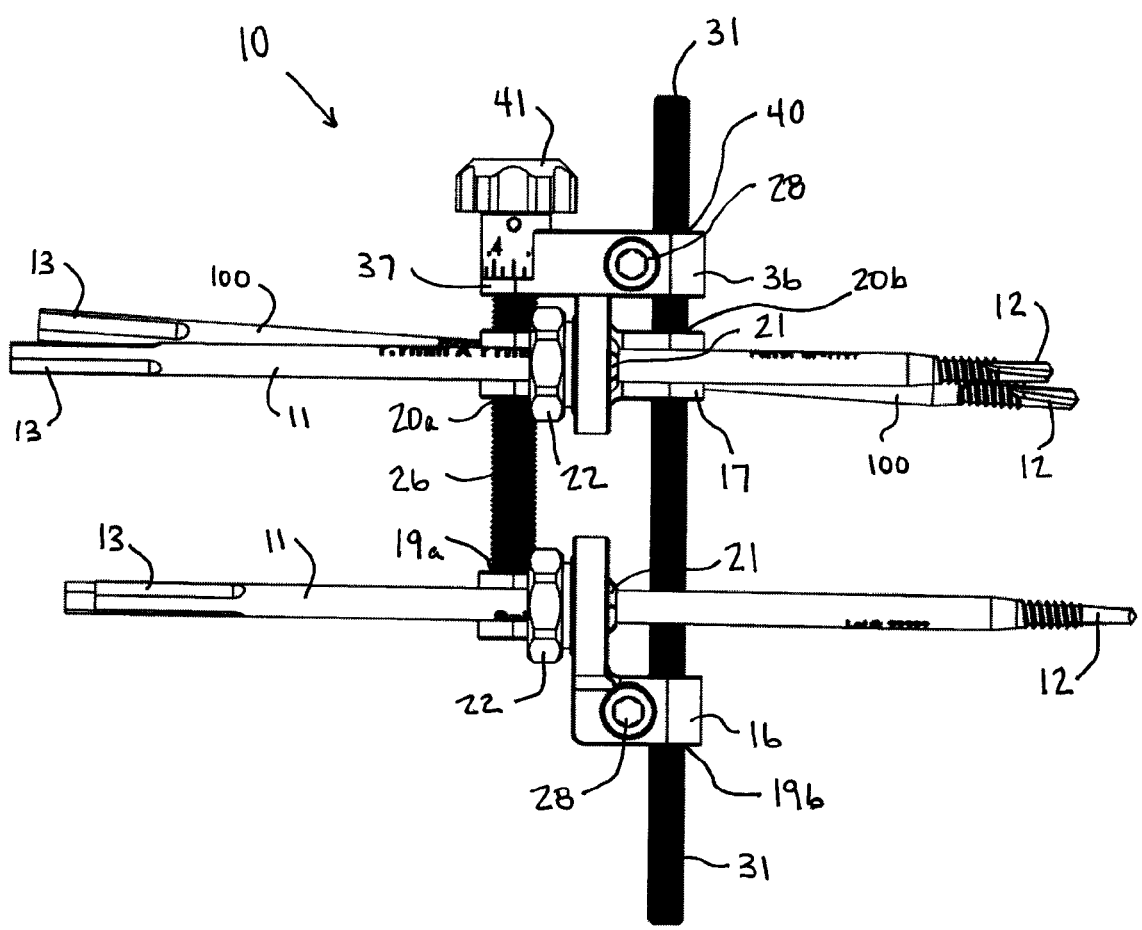
FIG. 4 is a right side elevational view of the present invention.
Figure 5:
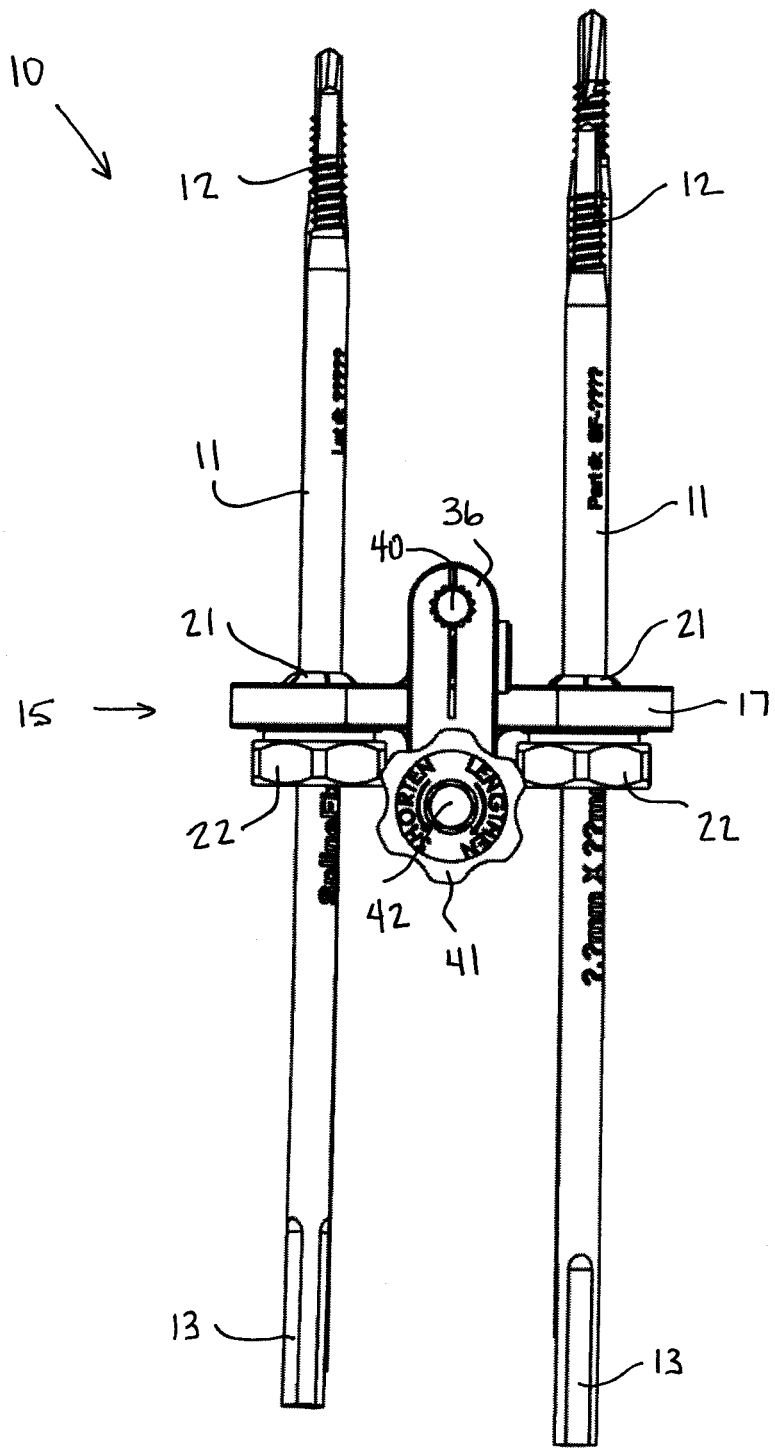
FIG. 5 is a top plan view of the present invention.
Figure 6:
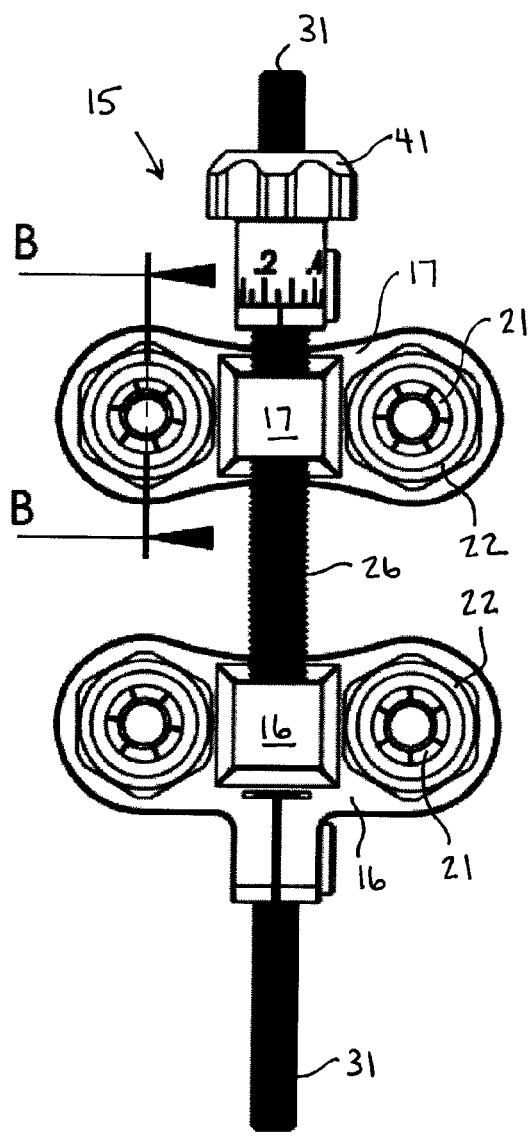
FIG. 6 is a front elevational view of the present invention.
Figure 7:
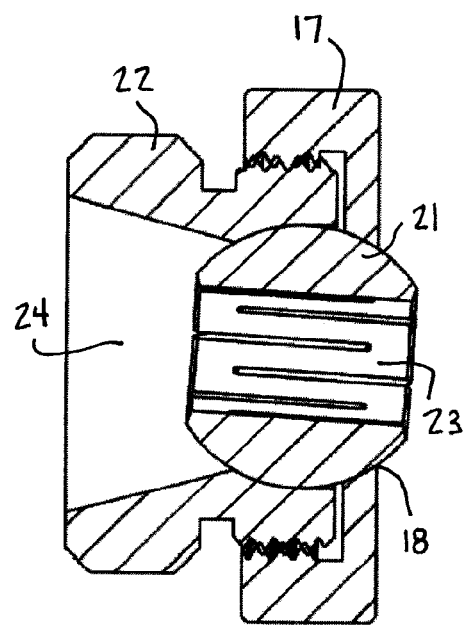
FIG. 7 is a sectional view taken along line B-B in FIG. 6.
Figure 8:
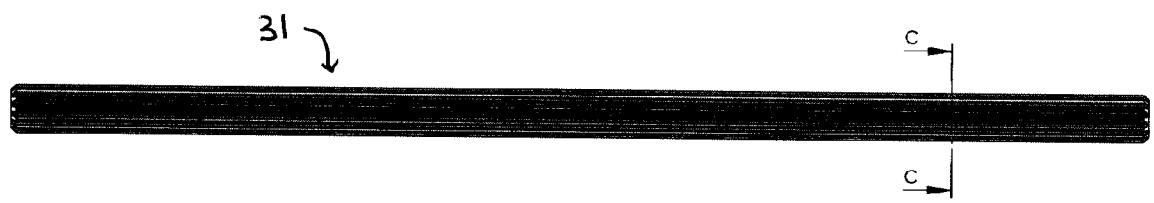
FIG. 8 is a side elevational view of the splined connector.
Figure 9:
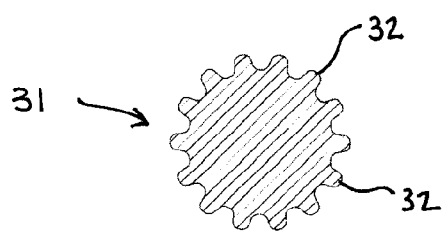
FIG. 9 is a sectional view of the splined connector taken along line C-C in FIG. 8.
Figure 10:
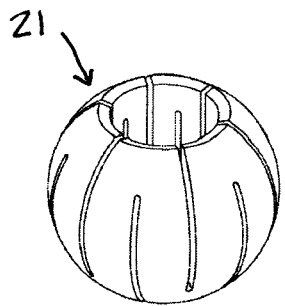
FIG. 10 is a perspective view of the ball collet.
Figure 11:
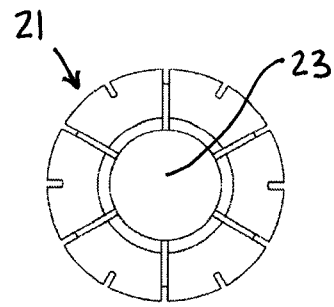
FIG. 11 is a top plan view of the ball collet.
Figure 12:
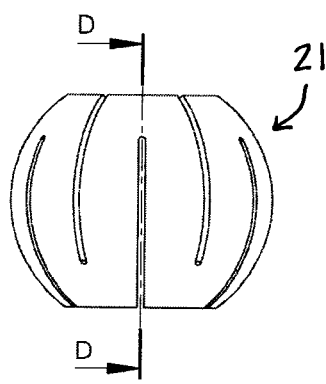
FIG. 12 is a side elevational view of the ball collet.
Figure 13:
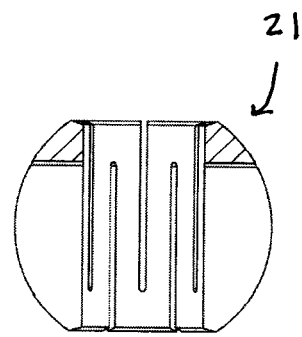
FIG. 13 is a sectional view of the ball collet taken along line D-D in FIG. 12.
Figure 14:
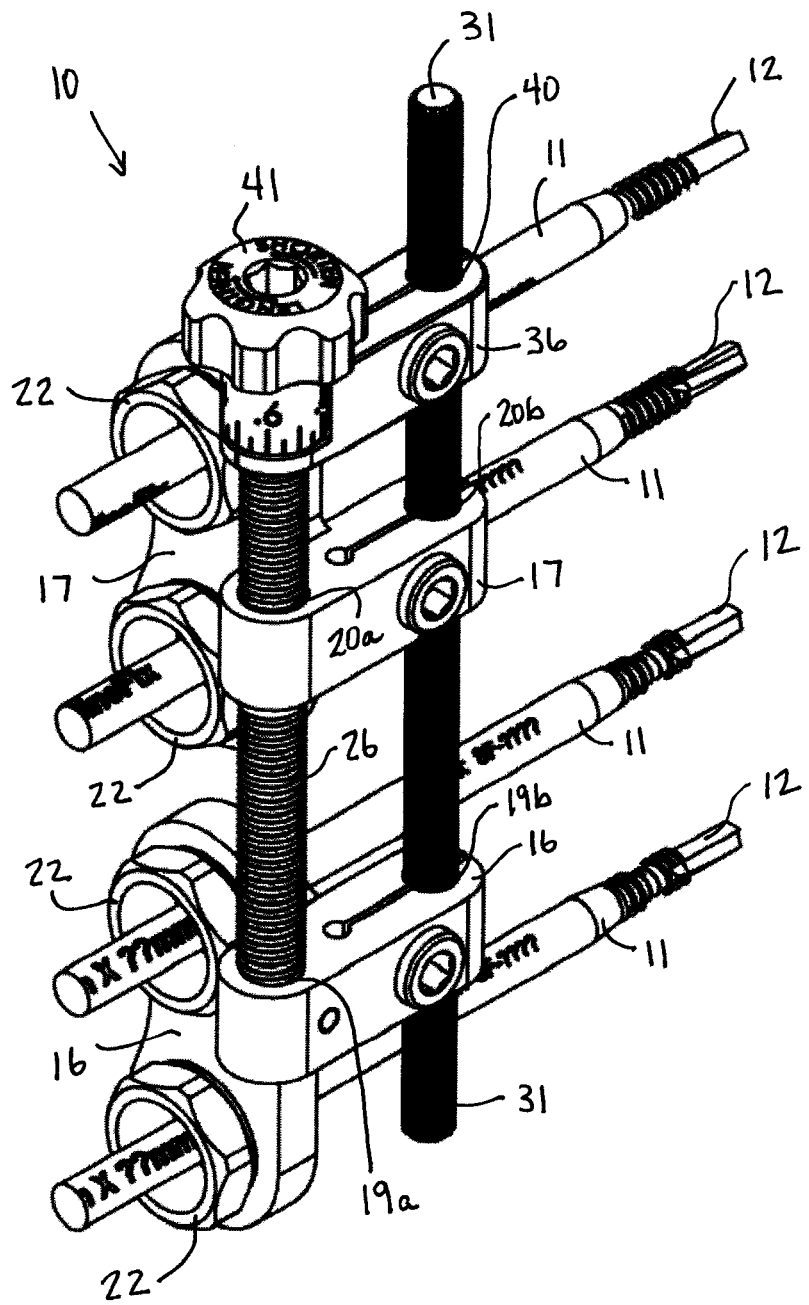
FIG. 14 is a right front perspective view of an alternate embodiment of the present invention.
Figure 15:
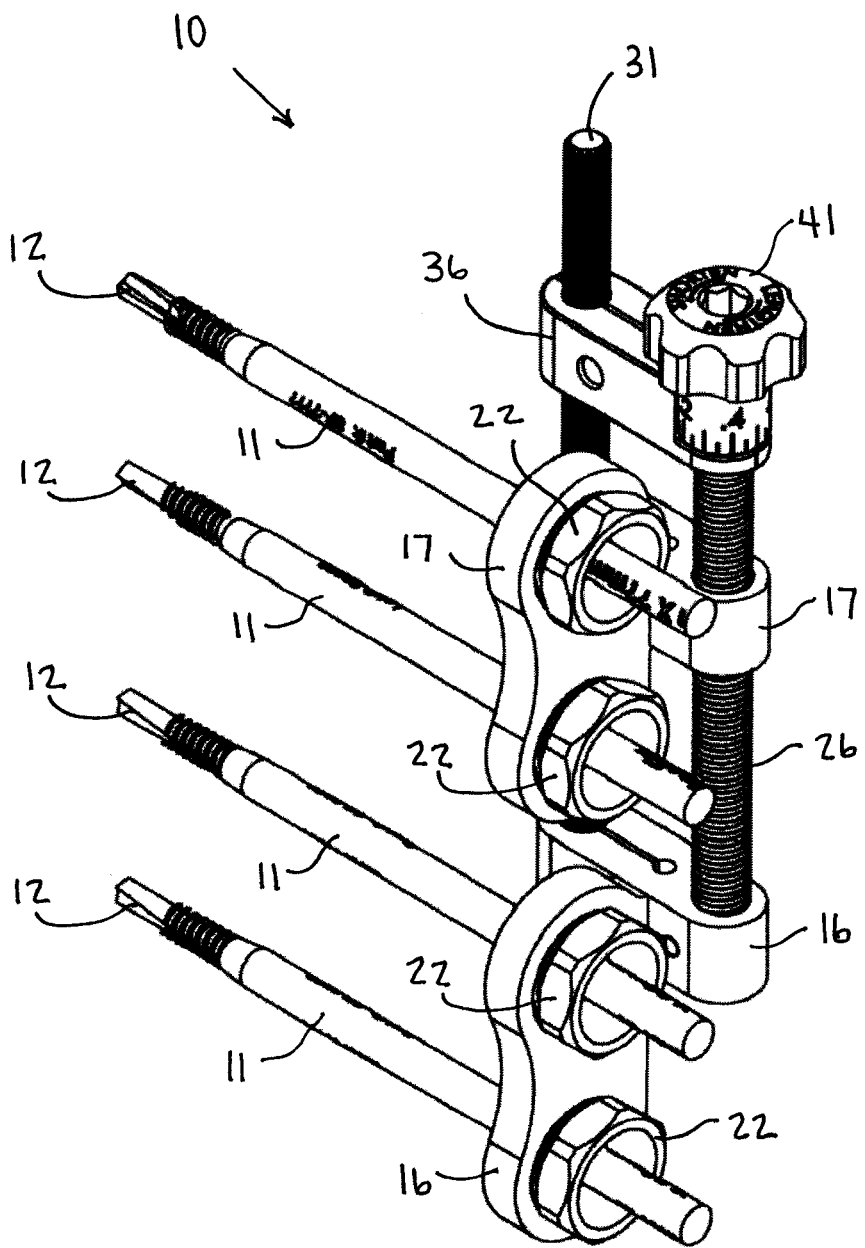
FIG. 15 is a left front perspective view of the embodiment of FIG. 14.
Figure 16:
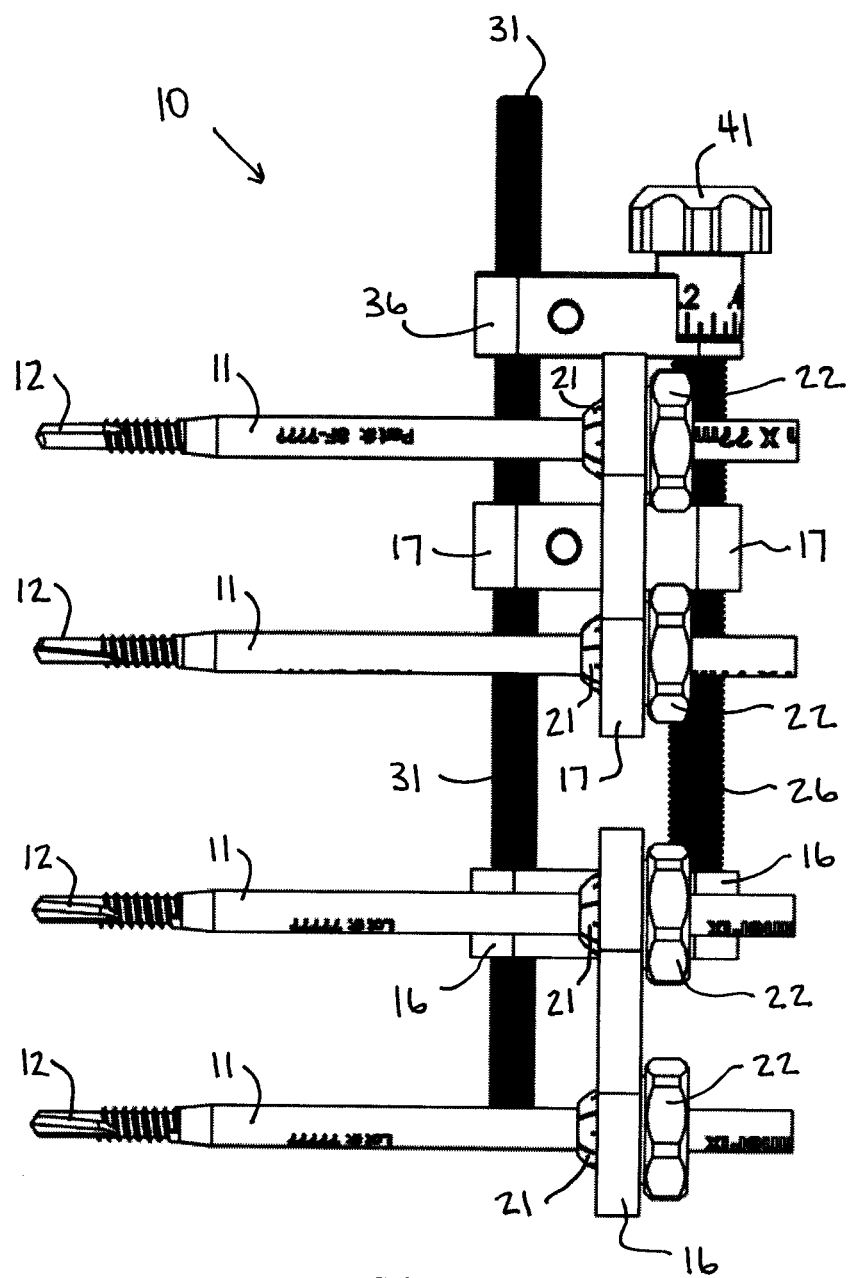
FIG. 16 is a left side elevational view of the embodiment of FIG. 14.
Figure 19:
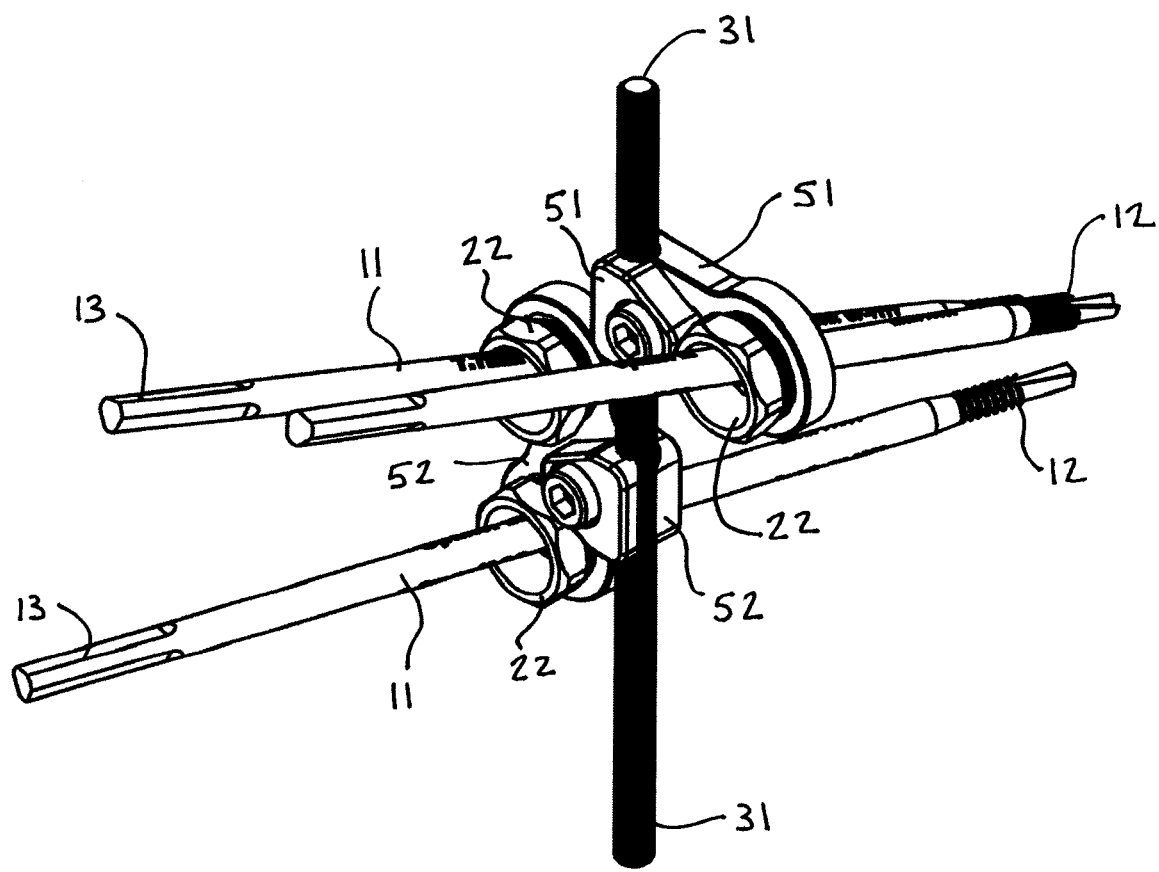
FIG. 19 is a right front perspective view of an alternate embodiment of the present invention.
Figure 20:
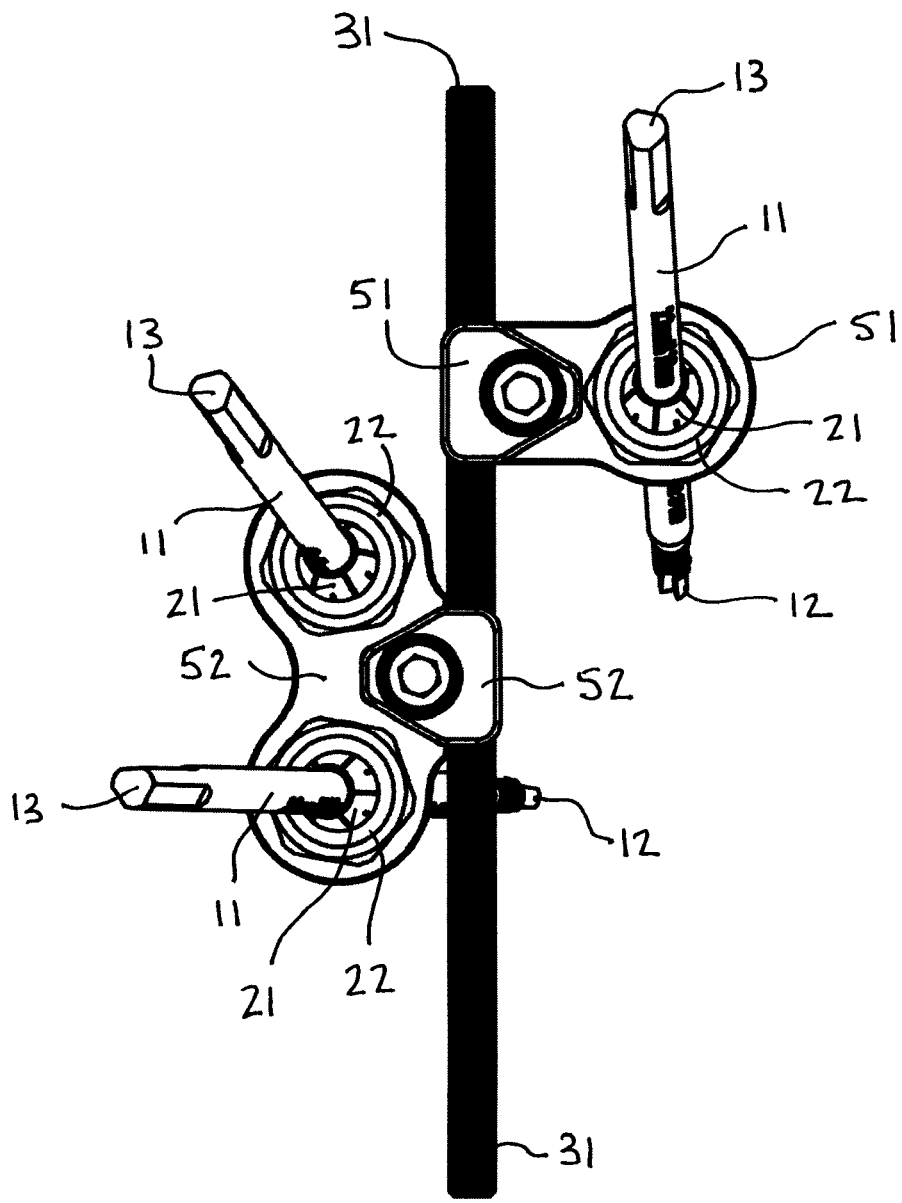
FIG. 20 is a front elevational view of the embodiment of FIG. 19.

Another principal feature of the invention is the collet feature, wherein use of the ball collets 21 allows for an expanded area for surgical pin 11 placement and enhances the accuracy of pin placement, with each pin having an independent range of motion. For example, FIG. 4 is a right side elevational view of the fixation apparatus 10 wherein pin 100 has been pivoted relative to the other pins 11 and is thus no longer in parallel relationship with them. Thus, the pins do not need to be held in parallel relationship with each other and in perpendicular relationship with the external frame assembly.

While the invention has been shown and described in some detail with reference to specific exemplary embodiments, there is no intention that the invention be limited to such detail. On the contrary, the invention is intended to include any alternative or equivalent embodiments that fall within the spirit and scope of the invention as described and claimed herein.

The invention claimed is:

1. An external fixation apparatus, comprising:
   a. a plurality of surgical pins, wherein each surgical pin has a first end for connecting to bone and an opposing second end;
   b. a plurality of ball collets, wherein each ball collet has an opening for receiving a surgical pin therethrough;
   c. a plurality of collet caps, wherein each collet cap has an opening for receiving a surgical pin therethrough;
   d. a drive screw having an upper end, a body, and a lower end;
   e. a connecting rod;
   f. a cap clamp having a first hole for receiving said upper end of said drive screw therethrough and a second hole for receiving said connecting rod therethrough;
   g. a movable clamp having a first hole for receiving said body of said drive screw therethrough, a second hole for receiving said connecting rod therethrough, and a first opening for receiving a surgical pin therethrough;
   h. a fixed clamp having a first hole for receiving said lower end of said drive screw therein, a second hole for receiving said connecting rod therethrough, and a first opening for receiving a surgical pin therethrough; and
   i. a drive knob having a hole for receiving said upper end of said drive screw therein;
   wherein said drive knob is secured to said drive screw for concomitant rotation therewith;
   j. wherein a first ball collet is pivotably mounted within said first opening of said movable clamp, wherein said first ball collet is secured within said first opening of said movable clamp by a first collet cap reversibly attached to said movable clamp, wherein a first surgical pin is pivotably mounted within said first ball collet;
   k. wherein a second ball collet is pivotably mounted within said first opening of said fixed clamp, wherein said second ball collet is secured within said first opening of said fixed clamp by a second collet cap reversibly attached to said fixed clamp, wherein a second surgical pin is pivotably mounted within said second ball collet; and
   l. wherein said drive knob is operable to rotate said drive screw and thereby move said movable clamp along the length of said body of said drive screw.

2. An external fixation apparatus according to claim 1, wherein said drive screw has an unthreaded upper end, a threaded body, and an unthreaded lower end.

3. An external fixation apparatus according to claim 1, wherein said connecting rod has a plurality of splines extending the length thereof.

4. An external fixation apparatus according to claim 1, wherein a third ball collet is pivotably mounted within a second opening of said movable clamp, wherein said third ball collet is secured within said second opening of said movable clamp by a third collet cap reversibly attached to said movable clamp, wherein a third surgical pin is pivotably mounted within said third ball collet.

5. An external fixation apparatus according to claim 4, wherein a fourth ball collet is pivotably mounted within a second opening of said fixed clamp, wherein said fourth ball collet is secured within said second opening of said fixed clamp by a fourth collet cap reversibly attached to said fixed clamp, wherein a fourth surgical pin is pivotably mounted within said fourth ball collet.

6. An external fixation apparatus, comprising:
- a. a plurality of surgical pins, wherein each surgical pin has a first end for connecting to bone, an opposing second end, and an elongated body;
- b. a plurality of ball collets, wherein each ball collet has an opening for receiving a surgical pin therethrough;
- c. a plurality of collet caps, wherein each collet cap has an opening for receiving a surgical pin therethrough;
- d. a drive screw having an unthreaded upper end, a threaded body, and an unthreaded lower end;
- e. a connecting rod having a plurality of splines extending the length thereof;
- f. a cap clamp having an unthreaded first hole for receiving said unthreaded upper end of said drive screw therethrough and a grooved second hole for receiving said connecting rod therethrough;
- g. a movable clamp having a threaded first hole for receiving said threaded body of said drive screw therethrough, a grooved second hole for receiving said connecting rod therethrough, and a first opening for receiving a surgical pin therethrough;
- h. a fixed clamp having an unthreaded first hole for receiving said unthreaded lower end of said drive screw therein, a grooved second hole for receiving said connecting rod therethrough, and a first opening for receiving a surgical pin therethrough; and
- i. a drive knob having a hole for receiving said unthreaded upper end of said drive screw therein; wherein said drive knob is secured to said drive screw for concomitant rotation therewith;
- j. wherein a first ball collet is pivotably mounted within said first opening of said movable clamp, wherein said first ball collet is secured within said first opening of said movable clamp by a first collet cap reversibly attached to said movable clamp, wherein a first surgical pin is pivotably mounted within said first ball collet;
- k. wherein a second ball collet is pivotably mounted within said first opening of said fixed clamp, wherein said second ball collet is secured within said first opening of said fixed clamp by a second collet cap reversibly attached to said fixed clamp, wherein a second surgical pin is pivotably mounted within said second ball collet;
- l. wherein a third ball collet is pivotably mounted within a second opening of said movable clamp, wherein said third ball collet is secured within said second opening of said movable clamp by a third collet cap reversibly attached to said movable clamp, wherein a third surgical pin is pivotably mounted within said third ball collet;
- m. wherein a fourth ball collet is pivotably mounted within a second opening of said fixed clamp, wherein said fourth ball collet is secured within said second opening of said fixed clamp by a fourth collet cap reversibly attached to said fixed clamp, wherein a fourth surgical pin is pivotably mounted within said fourth ball collet; and
- n. wherein said drive knob is operable to rotate said drive screw and thereby move said movable clamp along the length of said threaded body of said drive screw.

\* \* \* \* \*